US00PP19308P3

(12) United States Plant Patent
Levac

(10) Patent No.: US PP19,308 P3
(45) Date of Patent: Oct. 7, 2008

(54) *SPIRAEA* PLANT NAMED 'LEVGOLD'

(50) Latin Name: *Spiraea ×vanhouttei*
Varietal Denomination: Levgold

(76) Inventor: Denis Levac, 3800 Chemin Du Mont Sauvage, STE-Adele Quebec (CA), J8B 2E3

( * ) Notice: Subject to any disclaimer, the term of this patent is extended or adjusted under 35 U.S.C. 154(b) by 0 days.

(21) Appl. No.: 11/803,866

(22) Filed: May 16, 2007

(65) Prior Publication Data

US 2007/0271641 P1 Nov. 22, 2007

Related U.S. Application Data

(60) Provisional application No. 60/800,821, filed on May 16, 2006.

(51) Int. Cl.
*A01H 5/00* (2006.01)

(52) U.S. Cl. ..... Plt./226

(58) Field of Classification Search ..... Plt./226
See application file for complete search history.

(56) References Cited

PUBLICATIONS

UPOV–ROM GTITM, Plant Variety Database Jun. 2007, GTI Jouve Retrieval Software, citation for spiraea, 'Levgold'(1 page).*

* cited by examiner

*Primary Examiner*—Annette H Para
*Assistant Examiner*—S. B. McCormick-Ewoldt
(74) *Attorney, Agent, or Firm*—Penny J. Aguirre

(57) ABSTRACT

A new cultivar of *Spiraea×vanhouttei,* 'Levgold', characterized by its unique golden foliage on arching branches bearing abundant white umbellate corymbs along slender branches in late spring, its vigorous growth habit and cold hardiness.

2 Drawing Sheets

Botanical classification: *Spiraea×vanhouttei.*
Variety denomination: 'Levgold'.

BACKGROUND OF THE INVENTION

The present invention relates to a new and distinct cultivar of *Spiraea,* botanically known as *Spiraea×vanhouttei* 'Levgold' and will be referred to hereafter by its cultivar name, 'Levgold'. 'Levgold' is a new variety of bridal-wreath spirea for landscape use.

The inventor discovered 'Levgold' as a naturally occurring branch mutation of *Spiraea×vanhouttei* in June 1997 in a row of field grown plants in a nursery in Les Cedres, Quebec, Canada. 'Levgold' was selected as unique for the golden coloration of its foliage combined with cold hardiness.

Asexual reproduction of the new cultivar was first accomplished by the inventor using softwood stem cuttings in 1997 in Les Cèdres, Quebec, Canada. The characteristics of this cultivar have been determined both by stem cuttings and tissue culture to be stable and are reproduced true to type in successive generations.

SUMMARY OF THE INVENTION

The following traits have been repeatedly observed and represent the characteristics of the new cultivar as grown outdoors in a test plot for three years in Quebec, Canada. These attributes in combination distinguish 'Levgold' as a unique cultivar of *Spiraea.*

1. 'Levgold' has foliage that is golden yellow in coloration with color intensity highest when grown in full sun.

2. 'Levgold' blooms profusely with white flowers in umbellate clusters along the shoots in spring.
3. 'Levgold' has a compact, bushy habit with slender arching branches.
4. 'Levgold' is hardy to Canadian hardiness Zone 4.
5. 'Levgold' is a vigorous grower and readily propagated by stem cuttings and tissue culture.

'Levgold' is unique in comparisons to other cultivars of *Spiraea. Spiraea×vanhouttei,* the parent plant, has blue-green foliage whereas 'Levgold' have golden colored foliage. There are no cultivars of *Spiraea×vanhouttei* with golden foliage known to the inventor. The closest comparison plants are cultivars of other species of *Spiraea* with golden foliage. Cultivars of *Spiraea japonica* with golden foliage include; 'White Gold' (U.S. Plant Pat. No. 13,609) with golden foliage a white flowers, 'Lisp' (U.S. Plant Pat. No. 7,537) with golden foliage and pink flowers, and 'Golden Elf' (U.S. Plant Pat. No. 12,025) with golden foliage with a dwarf plant habit. 'Golden Carpet' (U.S. Plant Pat. No. 13,615) is a cultivar of *Spiraea×bumalda* and exhibits golden foliage with a compact, low mounding habit.

BRIEF DESCRIPTION OF THE DRAWING

The accompanying colored photographs illustrate the overall appearance and distinct characteristics of the new *Spiraea* as grown in Quebec, Canada for three years.

The photograph in FIG. 1 is a photograph depicts a typical plant in bloom.

Figure 1:
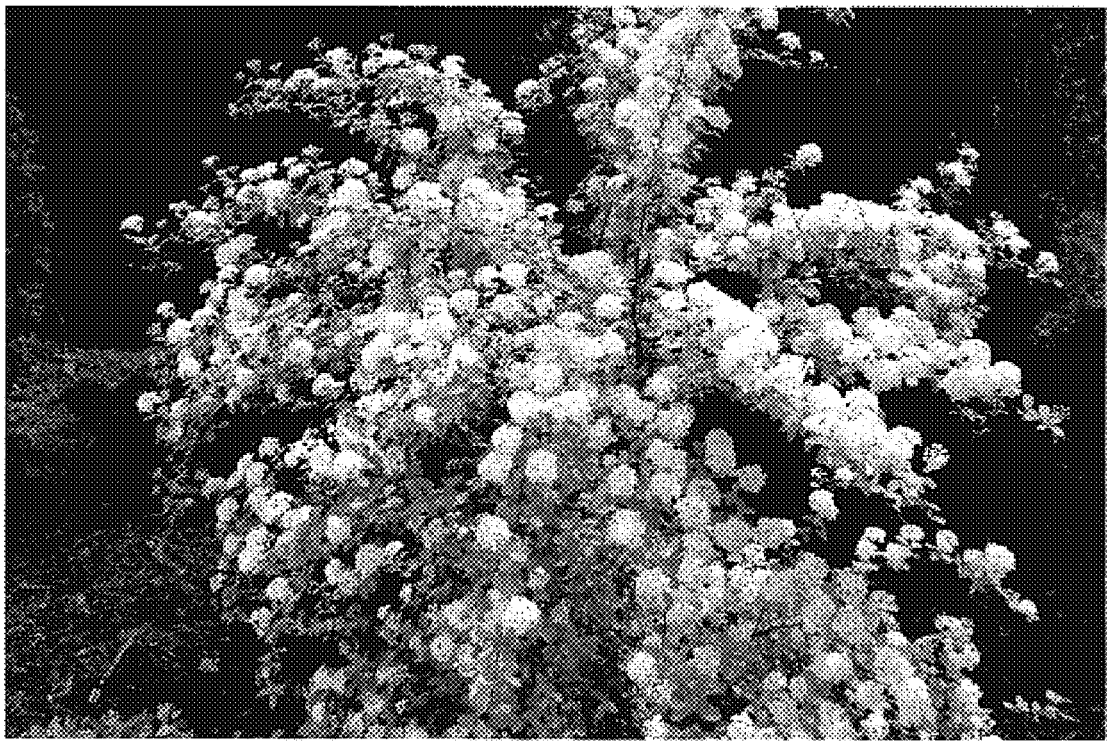
Figure 2:
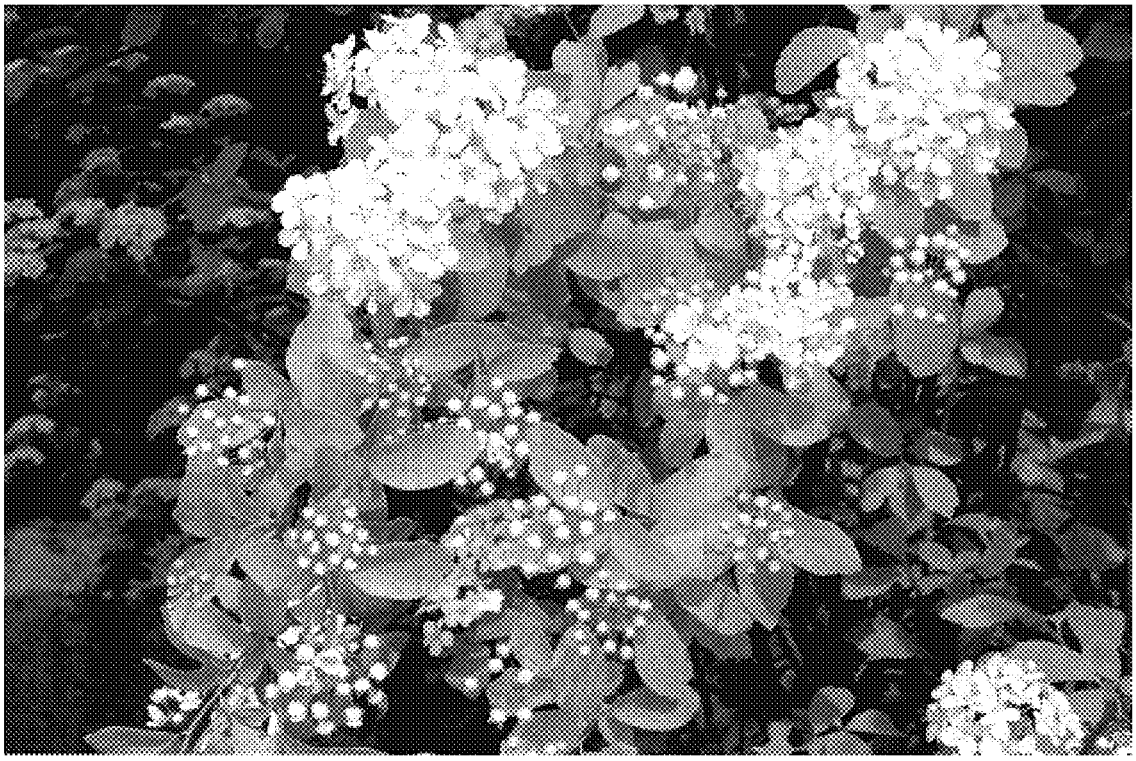

The photograph in FIG. 2 provides a close-up view of the foliage.

The colors in the photographs are as close as possible with the digital photography techniques available, the color values cited in the detailed botanical description accurately describe the colors of the new *Spiraea*.

DETAILED BOTANICAL DESCRIPTION

The following is a detailed description of the new cultivar as grown outdoors in partial shade in a trial garden in Quebec, Canada for three years. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General description:

*Botanical classification.*—'Levgold' is a cultivar of *Spiraea×vanhouttei*.

*Parentage.*—Naturally occurring branch mutation of an unnamed plants of *Spiraea×vanhouttei*.

*Blooming period.*—About two weeks in late spring on previous season's wood.

*Plant habit.*—Compact deciduous shrub with slender arching branches.

*Height and spread.*—Reaches about 1.2 m in height and about 1 m in width.

*Cold hardiness.*—Canadian Zone 4.

*Diseases and pests.*—No susceptibility or resistance to diseases or pests has been observed.

*Root description.*—Fibrous.

Growth and propagation:

*Propagation.*—Terminal, softwood stem cuttings and tissue culture.

*Growth rate.*—Vigorous.

Stem description:

*Shape.*—Round.

*Stem color.*—Young shoots 138C to 138D suffused with 165A to 165B, mature wood 165A.

*Stem size.*—Average of 2.7 mm and up to 120 cm in length.

*Stem surface.*—Glabrous.

*Internode length.*—Average of 1.3 cm.

*Branching.*—Medium density with secondary branches, tertiary branches minimal.

Foliage description:

*Leaf shape.*—Obovate to ovate.

*Leaf division.*—Simple.

*Leaf base.*—Cuneate.

*Leaf apex.*—Primarily acute.

*Leaf fragrance.*—None.

*Leaflet venation.*—Not prominent, pinnate, vein coloration matches leaf coloration.

*Leaflet margins.*—Bi-serrated on upper two third, entire near base.

*Leaf arrangement.*—Alternate.

*Leaf attachment.*—Petiolate.

*Leaf surface.*—Glabrous on upper surface and pubescent on lower surface.

*Leaf size.*—Average of 4.1 cm in length and 2.6 cm in width.

*Leaf quantity.*—About 40 on a branch 60 cm in length.

*Leaf color.*—Golden leaf coloration is most intense with sufficient sunlight, summer color when grown in full sun; 151D on upper and lower surface, summer color when grown in shade; 145B on upper and lower surface, fall color under all light conditions; 137B suffused with N167C on upper surface and 138B suffused with N167C on lower surface in fall.

*Petioles.*—About 7 mm in length, 1.5 mm in width, color 165A to 165B.

*Stipules.*—Absent.

Inflorescence description:

*Inflorescence type.*—Dense umbellate cormbs, present along stem on short laterals.

*Inflorescence size.*—About 4 cm in diameter and 2 cm in depth.

*Peduncles.*—About 7 cm in length and 1 mm in width, 144A in color, leafy with internodes about 1 cm with characteristics similar to stem leaves.

*Pedicels.*—About 1.5 cm in length and 0.5 mm in width, 144B in color, glabrous surface.

*Flower buds.*—Globose in shape, 3 mm in depth and diameter, 155A in color with sepal portion 144A.

*Flower fragrance.*—Absent.

*Persistence of flowers.*—Self-cleaning.

*Flower quantity.*—Average of 26 per secondary branch, average of 25 flowers per inflorescence.

*Lastingness of flowers.*—Each inflorescence lasts about 10 days with individual flowers lasting about 2 days.

*Flower type.*—Rotate.

*Flower aspect.*—Inflorescence cascades from upper surface of stem, flowers held upright to a 45° angle from peduncle.

*Flower size.*—About 1.3 cm in diameter and 3 mm in depth.

*Petals.*—5, about 4 mm in length and width, un-fused, orbicular in shape, rounded base, rounded apex with notch, whiter than 155A in color.

*Calyx.*—Star-shaped, flat aspect.

*Sepals.*—5, about 2 mm in length and 1.5 mm in width, fused base, ovate in shape, entire margins with fine hairs, 144A in color.

Reproductive organs:

*Pistils.*—5, filaments; 1 mm in length, 157 in color, stigmas; 0.3 mm in diameter, 160C in color, ovaries; superior; oblong in shape, 1 mm in length and width, 144A in color.

*Stamens.*—10, filaments; 2.5 mm in length, 155A in color, anthers; <0.3 mm in diameter, about 165A in color, pollen; moderate in quantity, 160B in color.

*Seed.*—Ovate and alate, less than 0.5 mm in diameter.

I claim:

1. A new and distinct cultivar of *Spiraea* plant named 'Levgold' as herein illustrated and described.

* * * * *